US010363400B2

(12) United States Patent
Lee et al.

(10) Patent No.: US 10,363,400 B2
(45) Date of Patent: Jul. 30, 2019

(54) METHOD TO MAKE TUBE-IN-TUBE BALLOON

(71) Applicant: BOSTON SCIENTIFIC SCIMED, INC., Maple Grove, MN (US)

(72) Inventors: Nao Lee, Brooklyn Park, MN (US); Ying Xiong, St. Paul, MN (US); Joe Khammoungkhoune, St. Michael, MN (US); John J. Chen, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 385 days.

(21) Appl. No.: 15/164,521

(22) Filed: May 25, 2016

(65) Prior Publication Data
US 2016/0263357 A1 Sep. 15, 2016

Related U.S. Application Data

(63) Continuation of application No. 13/459,793, filed on Apr. 30, 2012, now Pat. No. 9,370,638, which is a
(Continued)

(51) Int. Cl.
*A61M 25/10* (2013.01)
*B29C 48/09* (2019.01)
*A61L 29/04* (2006.01)
*A61L 29/14* (2006.01)
*A61M 25/00* (2006.01)
*B29C 49/04* (2006.01)
*B29C 49/22* (2006.01)
*B29C 65/48* (2006.01)
*B29C 65/00* (2006.01)
*B29C 55/26* (2006.01)
*B29C 65/14* (2006.01)
*B29C 35/08* (2006.01)
*B29K 23/00* (2006.01)
*B29K 33/20* (2006.01)
*B29K 55/02* (2006.01)
*B29K 67/00* (2006.01)
*B29K 71/00* (2006.01)
*B29K 75/00* (2006.01)
*B29K 77/00* (2006.01)
*B29K 96/00* (2006.01)
*B29K 105/00* (2006.01)
(Continued)

(52) U.S. Cl.
CPC ......... *A61M 25/1029* (2013.01); *A61L 29/04* (2013.01); *A61L 29/14* (2013.01); *A61M 25/0009* (2013.01); *B29C 48/09* (2019.02); *B29C 49/04* (2013.01); *B29C 49/22* (2013.01); *B29C 55/26* (2013.01); *B29C 65/48* (2013.01); *B29C 65/482* (2013.01); *B29C 65/4815* (2013.01); *B29C 65/4845* (2013.01); *B29C 66/52271* (2013.01); *B29C 66/63* (2013.01); *B29C 66/712* (2013.01); *B29C 65/1403* (2013.01); *B29C 65/1406* (2013.01); *B29C 65/484* (2013.01); *B29C 65/4825* (2013.01); *B29C 65/4835* (2013.01); *B29C 66/71* (2013.01); *B29C 2035/0827* (2013.01); *B29C 2035/0872* (2013.01); *B29K 2023/00* (2013.01); *B29K 2033/20* (2013.01); *B29K 2055/02* (2013.01); *B29K 2067/00* (2013.01); *B29K 2067/006* (2013.01); *B29K 2071/00* (2013.01); *B29K 2075/00* (2013.01); *B29K 2077/00* (2013.01); *B29K 2096/005* (2013.01); *B29K 2101/12* (2013.01); *B29K 2105/0079* (2013.01); *B29K 2105/0085* (2013.01); *B29K 2677/00* (2013.01); *B29L 2009/00* (2013.01); *B29L 2009/001* (2013.01); *B29L 2022/022* (2013.01); *B29L 2031/605* (2013.01); *B29L 2031/753* (2013.01); *B29L 2031/7542* (2013.01); *B29L 2031/7543* (2013.01); *Y10T 428/1352* (2015.01)

(58) Field of Classification Search
None
See application file for complete search history.

(56) References Cited

U.S. PATENT DOCUMENTS

| 4,427,744 A | 1/1984 | Hume, III |
| 4,906,244 A | 3/1990 | Pinchuk et al. |

(Continued)

FOREIGN PATENT DOCUMENTS

| EP | 0420488 A1 | 4/1991 |
| EP | 0768097 A2 | 4/1997 |

(Continued)

OTHER PUBLICATIONS

PCT Written Opinion for PCT/US06/44602, which claims priority to U.S. Appl. No. 11/366,257.

*Primary Examiner* — Monica A Huson
(74) *Attorney, Agent, or Firm* — Seager, Tufte & Wickhem LLP

(57) ABSTRACT

A tube-in-tube assembled parison for preparation of an elongated medical device. The parison if formed by assembling in tube-in-tube fashion a first tube of orientable polymer material and a second tube formed of orientable polymer material disposed around the first tube, with an adhesive tie layer disposed between the first and second tubes. The tubes are brought into contact to form a unitary parison. The adhesive may allow movement between the polymer layers during balloon blowing. The first tube, or the second tube, or both, may have been longitudinally pre-stretched after formation thereof but before assembly of the parison.

20 Claims, No Drawings

Related U.S. Application Data continuation of application No. 13/279,913, filed on Oct. 24, 2011, now Pat. No. 8,168,275, which is a continuation of application No. 11/366,257, filed on Mar. 2, 2006, now Pat. No. 8,043,673.

(51) Int. Cl.

| | | |
|---|---|---|
| B29L 9/00 | (2006.01) | |
| B29L 22/02 | (2006.01) | |
| B29L 31/60 | (2006.01) | |
| B29L 31/00 | (2006.01) | |
| B29K 101/12 | (2006.01) | |
| B29K 677/00 | (2006.01) | |

(56) References Cited

U.S. PATENT DOCUMENTS

| | | |
|---|---|---|
| 4,963,313 A | 10/1990 | Noddin et al. |
| 5,017,325 A | 5/1991 | Jackowski et al. |
| 5,087,394 A | 2/1992 | Keith |
| 5,096,848 A | 3/1992 | Kawamura |
| 5,195,969 A | 3/1993 | Wang et al. |
| 5,270,086 A | 12/1993 | Hamlin |
| 5,290,306 A | 3/1994 | Trotta et al. |
| 5,456,665 A | 10/1995 | Postell et al. |
| 5,478,320 A | 12/1995 | Trotta |
| 5,500,180 A | 3/1996 | Anderson et al. |
| 5,587,125 A | 12/1996 | Roychowdhury |
| 5,797,877 A | 8/1998 | Hamilton et al. |
| 5,879,369 A | 3/1999 | Ishida |
| 5,948,345 A | 9/1999 | Patel et al. |
| 6,004,289 A | 12/1999 | Saab |
| 6,042,930 A | 3/2000 | Kelch et al. |
| 6,124,007 A | 9/2000 | Wang et al. |
| 6,306,144 B1 | 10/2001 | Sydney et al. |
| 6,358,227 B1 | 3/2002 | Ferrera et al. |
| 6,465,067 B1 | 10/2002 | Wang et al. |
| 6,673,403 B1 * | 1/2004 | Shiiki ............... B29C 47/0023 428/35.7 |
| 6,696,121 B2 | 2/2004 | Jung, Jr. et al. |
| 6,753,379 B1 | 6/2004 | Kawate et al. |
| 6,863,861 B1 | 3/2005 | Zhang et al. |
| 6,951,675 B2 | 10/2005 | Chin et al. |
| 8,043,673 B2 | 10/2011 | Lee et al. |
| 8,168,275 B2 | 5/2012 | Lee et al. |
| 2001/0034386 A1 | 10/2001 | Scheibelhoffer et al. |
| 2003/0028211 A1 | 2/2003 | Crocker et al. |
| 2004/0267280 A1 | 12/2004 | Nishide et al. |
| 2005/0238833 A1 | 10/2005 | Wang et al. |

FOREIGN PATENT DOCUMENTS

| | | |
|---|---|---|
| WO | 9219316 A1 | 11/1992 |
| WO | 9604951 A1 | 2/1996 |
| WO | 02056930 A2 | 7/2002 |

\* cited by examiner

METHOD TO MAKE TUBE-IN-TUBE BALLOON

CROSS REFERENCE TO RELATED APPLICATIONS

This application is a continuation of U.S. application Ser. No. 13/459,793, filed on Apr. 30, 2012, which is a continuation of U.S. application Ser. No. 13/279,913, filed on Oct. 24, 2011, now U.S. Pat. No. 8,168,275, which is a continuation of U.S. application Ser. No. 11/366,257, filed on Mar. 2, 2006, now U.S. Pat. No. 8,043,673, all of which are herein incorporated by reference in their entirety.

FIELD OF THE INVENTION

The present invention pertains to an improved multilayer tube-in-tube balloon parison and to medical device balloons formed therefrom.

BACKGROUND OF THE INVENTION

Balloons mounted on the distal ends of catheters are widely used in medical treatment.

When medical device balloons are made by radial expansion of a tubular parison, there is typically a significant difference in the amount of orientation between the inner and outer layers of the balloon because the radial expansion of material on the outer side of the parison is typically significantly less than that of material at the inner side of the parison.

Multilayer balloons made from coextruded layers of different polymers are described in various patents including U.S. Pat. No. 5,270,086 (Hamlin); U.S. Pat. No. 5,195,969 (J. Wang, et al.); U.S. Pat. No. 5,290,306 (Trotta, et al); U.S. Pat. No. 5,879,369 (Ishida); and U.S. Pat. No. 5,797,877 (Hamilton et al).

As an alternative to a coextruded parison balloon, U.S. Pat. No. 6,004,289 (Saab) describes medical balloons made by a successive process of extruding a parison, blowing a very thin wall balloon of inelastic material such as high molecular weight PET, trimming away a portion of the balloon cone and the waist, replacing the trimmed balloon portion in the mold, placing a second full length parison in the mold, blowing a second thin-walled balloon of the same material inside the portion of the first balloon within the mold to produce a second balloon that has two layers in at least the body portion and a portion of the cone. Optionally the second balloon may be trimmed to remove at least its waist and a portion of the cone not covered by the first balloon portion and the remnant replaced in the mold. Following placement of a third parison of the same material in the mold and blowing the third parison into the remnant of the second balloon, a third thin-walled balloon that has staggered layers in the cone region, and three layers in the body region is produced. This iterative process produces a balloon in which each layer is separately biaxially oriented with a relatively smaller difference between the expansion of the inner and outer sides of the parison so that very high orientation prevails throughout the balloon body. However the procedure is extremely tedious and labor intensive.

A less labor intensive tube-in-tube balloon process for forming multi-layer balloons is described in U.S. Pat. No. 5,587,125 (Roychowdhury). Polymer tubes of different, closely fitting, sizes are prepared, one in slipped over and drawn down on the other to produce a tube-in-tube parison, and then the balloon is blown from that parison.

In U.S. Pat. No. 6,124,007 (L. Wang et al.), a tube-in-tube parison is prepared after at least one of the two polymer tubes has been longitudinally oriented by axial stretching. The layers may be the same or different. Radial expansion of the tube-in-tube parison gives a balloon in which there is separate orientation of the two layers so that substantial additional strength is provided to the laminate balloon. However, in some cases the balloon layers are poorly bonded and delamination of the balloon may occur at burst. This is undesirable.

SUMMARY OF THE INVENTION

The invention is directed to a tube-in-tube parison in which an adhesive layer is interposed between two tubes, and to novel balloons formed therefrom. In one aspect the invention is directed to a tube-in-tube assembled parison for preparation of an elongated medical device the parison comprising a first tube of orientable polymer material, a second tube formed of orientable polymer material disposed around the first tube, and an adhesive tie layer disposed between the first and second tubes and contacting the first and second tubes. The two tubes may be formed of the same material or different material and may be only part of a larger assembly of tubes used to make up the parison. The first tube, or the second tube, or both, may have been longitudinally pre-stretched after formation thereof but before assembly of the parison. Post-stretching of the parison after assembly may be performed before it is blown into a balloon.

A second aspect of the invention comprises a preferred method of making a laminate balloon which includes the steps of a) providing a first tube of a first polymer material, the first tube having an outer surface and an outer diameter; b) providing a second tube of a second polymer material, the second tube having an inner surface and an inner diameter greater than the outer diameter of the first tube; c) inserting the first tube into the second tube segment; d) bringing the second tube into direct annular contact with the first tube to form a laminate parison; and e) forming the laminate balloon by pressurizing the laminate parison at a temperature and pressure above ambient so as to expand the laminate parison structure, wherein, prior to the inserting step c), a layer of adhesive is provided on the outer surface of the first tube or on the inner surface of the second tube, or both, the total adhesive thickness still allowing tube-in-tube assembly of the parison.

Another aspect of the invention is a medical balloon formed by radial expansion of an assembled tubular parison of the invention.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The inventive balloon has better adhesion between the layers. Because of the adhesive tie layer, the layers are adhered to each other better and reinforce each other during inflation. The resulting balloon may have a higher burst pressure than the balloon without adhesive layer.

Further, the invention also reduces or prevents layer separation during balloon burst and afterwards as the device is withdrawn. With the balloons of the present invention there is a reduced chance that balloon fragments will escape into the body, thereby jeopardizing the safety of the patient.

The adhesive layer should be thin relative to the tubes employed in the parison formation. A parison thickness that provides 20% or less of the balloon wall thickness is desirable, preferably about 10% or less. A minimum thickness that will be effective to maintain lamination at burst is preferred. In some cases a molecular monolayer may be effective. For a typical catheter balloon of 1-10 mm diameter, the thickness of the adhesive may range from about 0.05 µm to about 2 µm.

Suitable adhesives may be formulated as hot-melt, emulsion, solvent or heat-curable adhesives. Relatively low melting hot-melt adhesives may be applied to one of the tubes after formation of the tube or it may be coextruded as a thin layer on one of the two tubes during tube formation. Emulsion adhesives have the advantage that they can be applied and dried to tack-free condition with little effect on most polymer substrates of interest.

In some embodiments, heat activated adhesives that soften, melt or cure at blowing temp but are sufficiently tack-free at room temp to allow the tube-in-tube parison to be readily assembled are employed. Examples of documents describing such adhesives include U.S. Pat. Nos. 4,427,744, 6,753,379, and 6,042,930. An antiblocking agent may be used to facilitate a tack-free surface prior to assembly.

Adhesives that are initially lubricious may also be used. A solvent-borne pressure sensitive adhesive (PSA) can be applied to one of the tubes, and the parison assembled right before molding and while the adhesive is still insufficiently tacky to substantially interfere with assembly of the parison. The residual solvent can act as lubricant during balloon molding. The material slides easily between the tubing surfaces during balloon molding and expanding process (with the presence of the solvent). The residual solvent will diffuse through thin wall polymer film of the balloon wall and evaporate from the surface of the balloon during or shortly after the molding process is complete.

This invention also simplified manufacture process because two tubes are no longer required to be as tightly fit to each other during the parison assembly process.

In another aspect the invention comprises a laminate balloon comprising at least two layers of separately oriented thermoplastic polymer material, coextensive over at least the body portion of the balloon and which are joined by an adhesive tie-layer in the coextensive portion.

The two layers may be the same or different polymer materials. The balloon may have an underlying layer made of a low compliant, high strength polymer and an overlying layer of a softer and more flexible polymer material relative to the first polymer material. Such balloons have good flexibility and surface softness, allowing catheters to track down into lesions relatively easily, good puncture resistance, good abrasion resistance and good refold characteristics, all contributed by the soft material top layer. Furthermore they also have a low compliance profile with high burst strength.

The inventive balloon structures may have an additive burst pressure, meaning that they are stronger than a first single-layer reference balloon corresponding to the underlying polymer layer. The additive strength of the balloons of the invention is exhibited typically by burst strengths greater than the first reference balloon by at least 50%, and in some embodiments at least 75%, of the strength of a second single-layer reference balloon corresponding to the overlying relatively soft flexible polymer layer. To obtain an additive strength it may be necessary to longitudinally orient both tubes before assembly of the parison. It may also be important to use an adhesive that allows for independent sliding of the parison layers during balloon molding, for instance by becoming active only when the adhesive temperature is near or above the temperature at which the parison begins to expand during the balloon blowing process. In some cases, the adhesive may not become activated until the balloon is heat set at a temperature higher than the blowing temperature.

The individual layers may be selected specifically for their contribution to the overall properties of the balloon. These properties may include burst strength, compliance, elasticity, abrasion and/or pinhole resistance, surface lubricity, surface softness or hardness, and bondability to materials to which the balloon is to be attached.

In some embodiments one or more layers the materials may be low compliant, high strength thermoplastic polymers. An example is poly(ethylene terephthalate) (PET) of initial intrinsic viscosity of at least 0.5, for instance, 0.7-1.3, as reported by the polymer manufacturer. Other high strength polyester materials, such as poly(ethylene napthalenedicarboxylate) (PEN), polybutylene naphthalate/phthalate copolyester such as Nouvelan®, sold by Teijin, Ltd., Japan, and polybutylene terephthalate (PBT); polyamides such as nylon 6, nylon 4/6, nylon 6/6, nylon 6/66, nylon 6/9, nylon 6/10, nylon 6/12, nylon 11 and nylon 12, and aromatic/aliphatic polyamides; thermoplastic polyimides; liquid crystal polymers or blend compositions containing liquid crystal polymers and high strength engineering thermoplastic polyurethanes such as Isoplast 301 sold by Dow Chemical Co., are considered suitable alternative materials. Physical blends and copolymers of such materials may also be used. A suitable thermoplastic polyimide is described in U.S. Pat. No. 5,096,848 and is available commercially under the tradename Aurum® from Mitsui Toatsu Chemicals, Inc., of Tokyo, Japan. Examples of liquid crystal polymers include the products Vectra® from Hoechst Celanese, Rodrun® from Unitika, LX or HX series polymers from DuPont and Xydar from Amoco.

Other polymers that a balloon layer may be formed from include ABS (acrylonitrile-butadiene-styrene) block copolymer, ABS/Nylon blends, ABS/polycarbonate blends and combinations thereof, styrene-acrylonitrile block copolymers, other acrylonitrile copolymers, polyacrylamide, polyacrylates, polyacrylsulfones polyester/polycaprolactone blends, polyetheretherketone (PEEK), polyethersulfone (PES), polyetherimide (PEI), polyetherketone (PEK), polymethylpentene, polyphenylene ether, polyphenylene sulfide, polyolefins such as polyethylene and polypropylene, olefin copolymers, such as ethylene-propylene copolymer, ethylene-vinyl acetate copolymers, ethylene-vinyl alcohol copolymers and polyolefin ionomers, polyvinyl chloride, polycaprolactam, N-vinyl-pyrrolidone, polyurethanes and polysiloxanes.

Still other suitable polymers for use in forming one or more layers of the balloons of the invention are thermoplastic elastomers, especially segmented polyester/ether block copolymers, such as available under the trademarks Arnitel® and Hytrel®; polyester-polyester block copolymers such as a polyester-polyester block copolymer having an aromatic polyester as the hard segment and an aliphatic polyester as the soft segment sold by Toyobo, under the trade names Pelprene S6001, Pelprene S9001; flexible polyurethanes, such as sold under the trademark Pellethane®; and polyamide/ether block copolymers (PEBA), such as sold under the Pebax® trademark. Particular examples include Arnitel® 740, Pebax® 7233, 7033 and 6333. The block copolymers in some embodiments may have a hardness, Shore D scale, of at least 50 and a flexural modulus of no more than about 150,000, in order to obtain good strength, compliance and softness characteristics. The Shore D hardness may be in the range of 50-75 and the flexural modulus may be in the range of 10,000-120,000.

In some embodiments the first and second tubes, independently, may be formed of a material selected from the group consisting of polyamide block copolymers, polyester block copolymers, polyesters, polyamides, polyurethanes, polyurethane block copolymers, polyetheretherketones, polyolefins, polyolefin ionomers, liquid crystal polymers, acrylonitrile polymers and copolymers, or a mixture or two or more thereof.

In accordance with the invention two different tubes are formed and processed into a parison. The tubes are extruded and, optionally, longitudinally stretched. The longitudinal stretching may be from 1× (no stretching) to about 2.5×, based on the original extruded tube length. This stretching process may be performed at ambient or higher temperature, for instance up to about 50° C. or even higher. At least one of the tubes is longitudinally stretched before the parison is assembled. In some cases all of the tubes may be longitudinally stretched before they are assembled together to form the balloon parison. The tubes may be pressurized internally during stretching. In some cases the internal pressure during longitudinal may be sufficient to maintain or expand the ID of the tube while the OD diminishes or stays the same.

If a hot melt adhesive is employed, the adhesive layer may be coextruded onto one of the mating surfaces of the polymer tubes. In such case the tube after any stretching processing is assembled tube-in-tube manner with the adhesive layer at the interface.

A hot melt adhesive may also be applied to a tube by spray application. Curable liquid, solvent borne or dispersion adhesives may be applied by spraying, dip coating, painting, or the like. If a solvent based adhesive is used it may be desirable to assemble the parison and blow the balloon before the solvent has fully evaporated in order to allow the individual layers of the parison to move independently during blowing. Low vapor pressure solvents may be desirable. Residual solvents typically can readily removed form the much thinner membrane of the formed balloon by subjecting the balloon during a residence aging time, which may be accelerated by ventilation with dry air, or an inert gas such as nitrogen and/or by subjecting the formed balloons to vacuum. In some cases heating during the balloon blowing step may be sufficient to drive residual solvent from the balloon.

Heat activatable aqueous dispersion adhesives are known that may be suitably employed in the invention. Such an adhesive is typically tack-free at ambient temperature, but softens and becomes adhesive when heated. Such an adhesive should be activatable at or below the maximum temperature encountered during the balloon blowing or a subsequent crystallization step. Heat activated adhesives may also be applied as solvent based adhesives. Curable liquid adhesives that are initiated or accelerated by heating may also be employed. Activation at too low a temperature, however, may not be desirable because the individual layers of the parison may not be able to move independently and premature bonding at the tube interfaces may not allow for optimal orientation of the individual layers. In at least some cases the heat activation temperature is above the glass transition temperature(s) of the polymer materials of the adjacent tubes.

If a curable adhesive is used it may be one that is activated to cure by exposure to heat during molding and/or heat setting or it may be one that is activated by mixing prior to application. Suitably it will cure sufficiently slowly to allow the parison layer to remain mobile relative to each other for at least a part of the time that the parison is being radially expanded to form the balloon.

A moisture curing adhesive may be used, with the coated tube suitably kept isolated from moisture prior to assembly of the parison. During balloon blowing, or after the balloon is blown, exposure of the curable adhesive to moisture may be accomplished by diffusion through the thin wall of the laminate. The moisture source may be a liquid water bath, a steam source, or even extended exposure to ambient humidity.

A UV or ionizing radiation curing adhesive may also be used. Suitably an assembly containing such an adhesive is not exposed to a UV source prior to blowing the balloon. During balloon blowing, or after the balloon is blown, the adhesive may be irradiated with UV or ionizing radiation through the inner or outer layer of the laminate, or both, with a fluence of radiation that is effective to initiate curing of the adhesive. Desirably the layer or layers through which the radiation is transmitted will have a low absorption of the relevant energy so that the radiation will penetrate to the adhesive layer and not negatively impact the layer polymer properties.

The adhesive, after curing, heat activation or solvent removal is one that is effective to hold the adjacent polymer layers together at human body temperature. Consequently the laminate will have a reduced tendency to fragment into unattached pieces if it is burst.

After the adhesive is in place, the parison is assembled by inserting the inner into the outer tube and drawing or necking down the outer tube by longitudinal stretching or thermal shrinking to bring it into direct contact with the inner tube. Two or more layers may be assembled in this way. A mandrel may be used to support the inner tube as the outer tube is drawn, necked or thermally shrunk onto the inner tube. Other techniques for assembly of tube-in-tube parisons as described in U.S. Pat. No. 5,587,125 (Roychowdhury) or U.S. Pat. No. 6,124,007 (L. Wang et al.) can also be adapted for use in the present invention by use of an adhesive as described herein.

Before blowing the assembled parison may be further processed by an additional longitudinal stretching step (post-stretching) if desired. Post-stretching may be particularly desirable in most cases where one or more of the individual tubes making up the parison were not stretched before assembly. By a combination of pre-assembly stretching of the individual layers and post-stretching, the individual layers may have an axial stretch ratio from 1.5 to 5.0×, and the ratio may be the same or different between the layers. In some cases one or more layers may have no longitudinal stretch ratio.

The parison may also be processed to thin regions of the parison that will become waist or cone and waist portions of the balloon. Known processes for thinning include grinding and necking of such regions.

To form the balloon, a conventional balloon forming process is suitably followed. In such a process the parison is typically heated at a mold temperature of from about 90° C. to about 120° C., for instance 90-110° C. with sufficient pressure to blow the parison to the mold dimensions. This may be a multi step process. In some cases longitudinal post-stretching may be performed concurrently with the blowing step. The balloon may be quenched after it has been blow formed or further processed with a heat set or shrinking/annealing step.

For heat setting, in some embodiments the balloon is transferred to a higher temperature bath, for instance 110°-150° C. with pressurization maintained, to enhance crystallization of the polymer of one or more layers. Typically such a process reduces balloon compliance. Alternatively a heat set may be accomplished dynamically by employing a mold temperature higher than the temperature needed to effectively blow the balloon at the pressure employed. In such a process the blowing step occurs before the parison material reaches the mold temperature so that holding the balloon in the mold until a time after its temperature has stabilized provides the desired crystallization enhancement without having to use a second molding apparatus or bath.

For a shrinking/annealing step the formed balloon may be held for a time at lower pressure and/or a temperature than the temperature employed for molding, for instance a temperature in the range of 70° C.-100° C. and pressure of 0-50 psi to modify the compliance curve of the balloon in a manner that enhances compliance by lowering the diameter that the balloon obtains at a low nominal inflation pressure.

Following balloon formation it is suitably mounted on an elongated catheter or endoscopic device or the like, prior to sterilization of the completed medical device. For stent delivery a stent may be mounted over the balloon mounted on a catheter before sterilization, or at the time of use in a surgical sterile field.

Balloons of the invention may be prepared for use on medical devices in various interventional medical specialties including cardiology, gastroenterology, pulmonary medicine, radiology, urology and vascular surgery. Examples of useful applications include catheters used in coronary and vascular percutaneous transluminal angioplasty, catheters used for ultrasound or laser imaging systems, catheters used to deliver and implant vascular prostheses, devices used to diagnose and treat gastrointestinal disorders, biliary interventional products used in endoscopic procedures in the gall bladder and bile ducts, and prostrate dilatation catheters. Depending on the particular application, the balloons may be prepared with a wide range of inflated diameters, typically in the range of 1 mm to about 30 mm, and more typically 1.5 mm to about 20 mm, with typical lengths ranging from 5 mm to about 100 mm.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

What is claimed is:

1. A method of making an expandable medical balloon, comprising:
   disposing an adhesive layer on a tubular parison, the tubular parison comprising polyamide, poly(ether-block-amide), or a combination thereof; and
   longitudinally pre-stretching the tubular parison from a first length to a second length; and
   radially expanding the tubular parison in a balloon mold, wherein the radial expansion comprises pressuring the assembly at a temperature and a pressure above ambient temperature or up to about 50° C. so as to expand the parison into a medical balloon, the parison having a wall thickness $T_a$ and the medical balloon having a wall thickness $T_b$.

2. The method of claim 1, wherein the disposing step comprises coextruding the adhesive layer with the tubular parison.

3. The method of claim 1, wherein the second length is about 2.5 times greater than the first length.

4. The method of claim 1, wherein the tubular parison has been longitudinally pre-stretched and wherein the second length is about 1.0 times to about 2.5 times greater than the first length.

5. The method of claim 1, wherein the adhesive layer provides 20% or less of the tubular parison wall thickness.

6. The method of claim 1, wherein the adhesive layer provides 10% or less of the tubular parison wall thickness.

7. The method of claim 1, wherein the adhesive layer has a thickness that is about 0.05 μm to about 2 μm.

8. The method of claim 1, wherein the tubular parison comprises poly(ether-block-amide).

9. The method of claim 1, wherein the adhesive comprises thermoplastic, emulsion, solvent or curable compositions.

10. The method of claim 1, wherein the adhesive comprises a thermoplastic adhesive.

11. The method of claim 1, wherein the tubular parison comprises an underlying layer formed of poly(ether-block-amide) and an overlying layer formed of polyamide.

12. The balloon of claim 1, wherein the adhesive layer has a thickness $T_a$ that is 10% or less of the balloon wall thickness $T_b$.

13. A method of making an expandable medical balloon, comprising:
   disposing a thermoplastic adhesive on a tubular parison, the tubular parison comprising a first polymer having a Shore D hardness of about 50 to about 75; and
   longitudinally pre-stretching the tubular parison from a first length to a second length; and
   radially expanding the tubular parison in a balloon mold, wherein the radial expansion comprises pressuring the assembly at a temperature and a pressure above ambient temperature or up to about 50° C. so as to expand the parison into a medical balloon, the parison having a wall thickness $T_a$ and the medical balloon having a wall thickness $T_b$.

14. The method of claim 13, further comprising radially expanding the tubular parison in a balloon mold.

15. The method of claim 13, wherein the tubular parison comprises an underlying layer comprising a second polymer having a Shore D hardness that is higher than the first polymer, the method further comprising radially expanding the tubular parison in a balloon mold.

16. The method of claim 13, wherein the tubular parison has been longitudinally pre-stretched and wherein the second length is about 2.5 times greater than the first length.

17. The method of claim 15, wherein the underlying layer comprises poly(ether-block-amide) and the overlying layer comprises nylon.

18. The method of claim 13, wherein the disposing step comprises coextruding the thermoplastic adhesive and the tubular parison.

19. A method of making an expandable medical balloon, comprising:
- disposing an adhesive layer on a tubular parison, the tubular parison comprising polyamide, poly(ether-block-amide), or a combination thereof;
- longitudinally pre-stretching the tubular parison from a first length to a second length; and
- radially expanding the tubular parison in a balloon mold so as to form the parison into a medical balloon having a balloon wall thickness $T_b$,
- wherein the adhesive layer has a thickness $T_a$ that is 20% or less of the balloon wall thickness $T_b$.

20. The balloon of claim 19, wherein the adhesive layer has a thickness $T_a$ that is 10% or less of the balloon wall thickness $T_b$.

* * * * *